US007863335B2

(12) United States Patent
Fan

(10) Patent No.: US 7,863,335 B2
(45) Date of Patent: Jan. 4, 2011

(54) NON-ANTIBIOTIC INTERVENTION OF CHLAMYDIAL INFECTION

(75) Inventor: Huizhou Fan, Edison, NJ (US)

(73) Assignee: The University of Medicine and Dentistry of New Jersey, New Brunswick, NJ (US)

( * ) Notice: Subject to any disclaimer, the term of this patent is extended or adjusted under 35 U.S.C. 154(b) by 638 days.

(21) Appl. No.: 11/572,546

(22) PCT Filed: Jul. 25, 2005

(86) PCT No.: PCT/US2005/026333

§ 371 (c)(1), (2), (4) Date: Oct. 11, 2007

(87) PCT Pub. No.: WO2006/025978

PCT Pub. Date: Mar. 9, 2006

(65) Prior Publication Data

US 2008/0075758 A1 Mar. 27, 2008

Related U.S. Application Data

(60) Provisional application No. 60/590,799, filed on Jul. 23, 2004.

(51) Int. Cl.

| | |
|---|---|
| ***A01N 33/24*** | (2006.01) |
| ***A01N 35/00*** | (2006.01) |
| ***A01N 43/38*** | (2006.01) |
| ***A61K 31/13*** | (2006.01) |
| ***A61K 31/12*** | (2006.01) |
| ***A61K 31/40*** | (2006.01) |
| ***A61F 6/06*** | (2006.01) |
| ***A61F 13/00*** | (2006.01) |

(52) U.S. Cl. ....................... 514/645; 514/419; 514/682; 424/433; 424/422; 424/430

(58) Field of Classification Search ....................... None
See application file for complete search history.

(56) References Cited

U.S. PATENT DOCUMENTS

| | | | |
|---|---|---|---|
| 4,446,860 | A | 5/1984 | Gutnick |
| 2003/0113726 | A1 | 6/2003 | Tsuchihashi et al. |
| 2004/0235886 | A1 | 11/2004 | Charifson et al. |

OTHER PUBLICATIONS

Ault et al. "Chlamydia trachomatis enhances the expression of matrix metalloproteinases in an in vitro model of the human fallopian tube infection" Am J Obstet Gynecol, Nov. 2002, vol. 187, pp. 1377-1383.*

Brown, P.D. "Matrix metalloproteinase inhibitors" Angiogenesis, 1997, vol. 1, pp. 142-154.*

Duesbery, N.S. et al., Proteolytic Inactivation of MAP-Kinase-Kinase by Anthrax Lethal Factor, J. Science, May 1, 1998, pp. 734-737, vol. 280.

Fan, H. et al., Characterization of Growth Factor-induced Serine Phosphorylation of Tumor Necrosis Factor-alpha Converting Enzyme and of an Alternatively Translated Polypeptide, J. Biological Chemistry, May 16, 2003, pp. 18617-18627, vol. 278, No. 20.

Fan, H. et al., Acquisition and Synthesis of Folates by Obligate Intracellular Bacteria of the Genus Chlamydia, J. Clinical Investigation, Nov. 1992, pp. 1803-1811, vol. 90.

Fan. H. et al., Biochemical Evidence for the Existence of Thymidylate Synthase in the Obligate Intracellular Parasite Chlamydia trachomatis, J. Bacteriology, Nov. 1991, pp. 6670-6677, vol. 173, No. 21.

Levy D.E. et al., Matrix Metalloproteinase Inhibitors: A structure—Activity Study, J. Med. Chem., Jan. 15, 1998, pp. 199-223, vol. 41.

Lopez-Otin, C. et al., Protease Degradomics: A New Challenge for Proteomics, Nature Reviews: Molecular Cell Biology, Jul. 2002, pp. 509-519, vol. 3.

Moulder, J.W., Interaction of Chlamydiae and Host Cells In Vitro, Microbiological Reviews, Mar. 1991, pp. 143-190, vol. 55, No. 1.

Oguma, K. et al., Structure and Function of *Clostridium botulinum* Toxins, Microbiological Immunology, 1995, pp. 161-168, vol. 39, No. 3.

Schachter, J., Chapter 6: Infection and Disease Epidemiology in Chlamydia: Intracellular Biology, Pathogenesis, and Immunity, Edited by R.S. Stephens, 1999, pp. 139-169, American Society for Microbiology, Washington D.C.

Steele-Mortimer, O. et al., The invastion-associated Type III Secretion System of *Salmonella enterica* serovar Typhimurium is Necessary for Intracellular Proliferation and Vacuole Biogenesis in Epithelial Cells, J. Cellular Microbiology, 2002, pp. 43-54, vol. 4, No. 1.

Stephens, R. S. et al., Genome Sequence of an Obligate Intracellular Pathogen of Humans: *Chlamydia trachomatis*, J. Science, Oct. 23, 1998, pp. 754-759, vol. 282.

Zhong, G. et al., Identification of a Chlamydial Protease-like Activity Factor Responsible for the Degradation of Host Transciption Factors, J. Exp. Med., Apr. 16, 2001, pp. 935-942, vol. 193, No. 8.

Kontogiorgis, C.A. et al., "Matrix Metalloproteinase Inhibitors: A Review on Pharmacophore Mapping and (Q)Sars Results", Current Medicinal Chemistry, 2005, vol. 12, pp. 339-355.

Chen, S. et al., "Universal Screening or Prophylactic Treatment for Chlamydia trachomatis Infection Among Women Seeking Induced Abortionis: Which Strategy is More Cost-Effective?", Sexually Transmitted Diseases, Apr. 2007, vol. 34, No. 4, pp. 230-236.

* cited by examiner

*Primary Examiner*—Sreeni Padmanabhan
*Assistant Examiner*—Kendra D Carter
(74) *Attorney, Agent, or Firm*—Fox Rothschild LLP; Peter J. Butch, III; Shahnam Sharareh

(57) ABSTRACT

Methods for treating or reducing the risk of transmission of *chlamydia* to a recipient by topically applying a metalloprotease inhibitor to a site on the recipient which is likely to be exposed to *Chlamydia*. Topical compositions containing metalloprotease inhibitors are also disclosed for treating or reducing the risk of transmission of *Chlamydia*, as well as barrier contraceptive devices coated therewith.

12 Claims, 6 Drawing Sheets

No (pre)treatment | HeLa pretreated | EBs pretreated | Treated

Figure 6. Intracellular Targeting of *Chlamydia* by GM6001.

| | No GM6001 | GM6001 added at hours after infection | | |
|---|---|---|---|---|
| | | 2 | 8 | 24 |
| IFUs | $5.2 \times 10^7$ | $1.4 \times 10^2$ | $5.5 \times 10^2$ | $5.2 \times 10^5$ |
| % inhibition | 0 | >99.99 | >99.99 | 99 |

GM6001 (final concentration: 20 μM) was added to L2-infected HeLa cell cultures at indicated time points. Cells were lysed at 40 h after infection. The inclusion-forming units (IFUs) of released EBs were titrated on HeLa cells with MOMP immunofluorescence microscopy.

NON-ANTIBIOTIC INTERVENTION OF CHLAMYDIAL INFECTION

CROSS-REFERENCE TO RELATED APPLICATIONS

This application is a National Stage of International Application No. PCT/US2005/026333, filed Jul. 25, 2005, which claims priority under 35 U.S.C. §119(e) to U.S. Provisional Application Ser. No. 60/590,799, which was filed on Jul. 23, 2004, the disclosures of both of which are incorporated herein by reference.

BACKGROUND OF THE INVENTION

*Chlamydiae* are Gram-negative eubacteria that replicate inside eukaryotic cells. They are wide-spread pathogens responsible for, or contributing to, many diseases including preventable blindness, pneumonia, pelvic inflammatory disease, infertility, arthritis, and cardiovascular disease in humans.

*Chlamydia trachomatis* is an obligate intracellular pathogen consisting of three biovars. Biovar trachoma is responsible for preventable blindness, and is also a major cause of sexually transmitted infections characterized by cervicitis, endometritis and salpingitis in women, and urethritis in men, whereas biovar lymphogranuloma venereum (LGV) causes a more invasive sexually transmitted syndrome that attacks subepithelial and lymphatic tissues. Biovar mouse is not a human pathogen; however, it is a useful organism modeling human chlamydial infection in mice.

*Chlamydiae* including *C. trachomatis* have a unique developmental cycle, which begins with attachment of an infectious elementary body (EB) to the host cell that internalizes the bacterium into a vacuole termed inclusion. In the inclusion, the EB differentiates into the non-infectious, metabolically active reticulate body (RB), which replicates by binary fission. Around the midpoint of the developmental cycle, the majority of RBs start to reorganize back to EBs which are then released to infect additional cells. Mammalian cells express a wide range of metalloproteases; many of them are inhibited by hydroxamates. The molecular mechanisms underlying the intracellular development of *Chlamydiae* remain largely undefined.

Infection by members of the genus *Chlamydiae* induces significant inflammatory responses. For example, genital lesions produced by *Chlamydia trachomatis* frequently elicit a vigorous influx of lymphocytes, macrophages, and plasma cells, suggesting the development of humoral and cellular immunity. Yet, clinically, the initial infection is frequently varied in symptomatology and may even be asymptomatic. Once fully established, the *Chlamydia* are difficult to eradicate, with frequent relapse following antibiotic therapy.

In view of the chronic and persistent nature of chlamydial infections, there is a need for reliable methods for the prevention of pathogenic infection as well as therapeutic approaches to manage the infection.

SUMMARY OF THE INVENTION

We have determined that hydroxamate-based inhibitors of metalloproteases are potent inhibitors of chlamydial infection in vitro and in vivo, whereas they are ineffective against common bacteria. A chlamydial mutant that is less resistant to the inhibitors has been isolated, suggesting that the compounds block the intracellular development of *Chlamydia* by targeting chlamydial metalloprotease activity. Thus, chlamydial metalloprotease activity plays an essential role in chlamydial infection, and is a novel preventive and therapeutic target because its inhibition will not cause other bacteria to resist common antibiotics, and will unlikely disturb normal microbial flora as classical antibiotics do.

One aspect of the present invention provides a method for prophylactically reducing the risk of transmission of *Chlamydia* to a recipient by topically applying a composition containing a *Chlamydia* prophylactic effective amount of a metalloprotease inhibitor to a site on the recipient which is likely to be exposed to *Chlamydia*. Another aspect of the present invention provides a method for treating chlamydial infection by applying a treatment effective amount of a metalloprotease inhibitor to a portion of a patient's body infected by *Chlamydia*. Another aspect of the present invention provides a barrier contraceptive device for reducing the risk of transmission of *Chlamydia* characterized in that the barrier contraceptive device is coated with a metalloprotease inhibitor composition. A further aspect of the present invention provides a topical composition containing a metalloprotease inhibitor composition.

In one embodiment, the metalloprotease inhibitor is selected from the group consisting of N-[(2R)-2-(hydroxamidocarbonylmethyl)-4-methylpentanoyl]-L-typtophan methylamide and N-(R)-[2-(hydroxyaminocarbonyl)methyl]-4-methylpentanoyl-L-naphthylalanyl-L-alanine amide.

In another embodiment, the metalloprotease inhibitor is incorporated into a pharmaceutically acceptable aqueous solution, non-aqueous solution, suspension, ointment, jelly, insert, suppository, foaming suppository, sponge, salve, cream, foam, foaming tablet, or douche. In a further embodiment, the metalloprotease inhibitor is applied with an applicator, which may be a barrier contraceptive device such as male condoms, female condoms, diaphragms, cervical caps, and the like.

In an additional embodiment, the chlamydial infection is selected from the group consisting of chlamydial eye diseases, sexually transmitted chlamydial infections, complications of sexually transmitted chlamydial infections, and chlamydial pneumonia.

BRIEF DESCRIPTION OF THE DRAWINGS

FIG. 1A is MOMP immunofluorescence microscopy results showing a dose-dependent inhibition of inclusion formation in L2-infected HeLa cells treated with GM6001;

FIG. 1B is a dot blot analysis of MOMP revealing inhibition of L2 growth in A549 cells by GM6001 (circled is the area that was loaded with GM6001-treated sample, but yielded no MOMP signal);

FIG. 2A is immunostaining of chlamydial lipopolysaccharide demonstrating inhibition by GM6001 of inclusion formation in HeLa cells infected with serovar D (biovar trachoma);

FIG. 2B shows dose dependent inhibition of MoPn (biovar mouse) DNA synthesis by GM6001 (all analyses were made with triplicate wells; results varied less than 15%);

FIG. 3A is an immunofluorescence assay showing inhibition of L2 inclusion formation in HeLa cells by TAPI-0;

FIG. 3B is a graph demonstrating that there are no effects of TAPI-0 on HeLa cell DNA synthesis (analyses were made with triplicate wells; results varied less than 7%);

FIG. 3C is a dot blot analysis demonstrating the failure of GM-NC to inhibit L2 growth in HeLa cells (circled are areas loaded with either GM6001-treated L2-infected sample or uninfected HeLa cell lysate that yielded no MOMP signals);

FIG. 3D is a graph showing the lack of effects of GM-NC on HeLa cell DNA synthesis. (analyses were made with triplicate wells; results varied less than 7%);

FIG. 4A is a graph of $OD_{600}$ versus mM TAPI for *Escherichia coli;*

FIG. 4B is a graph of $OD_{600}$ versus Time (hours) for *Lactobacillus delbrueckii;*

FIG. 4C is a graph of $OD_{600}$ versus Time (hours) for *Salmonella enterica;*

FIG. 6 is a table relating to the intracellular targeting of *Chlamydia* by GM6001.

DETAILED DESCRIPTION OF THE INVENTION

Figure 1:
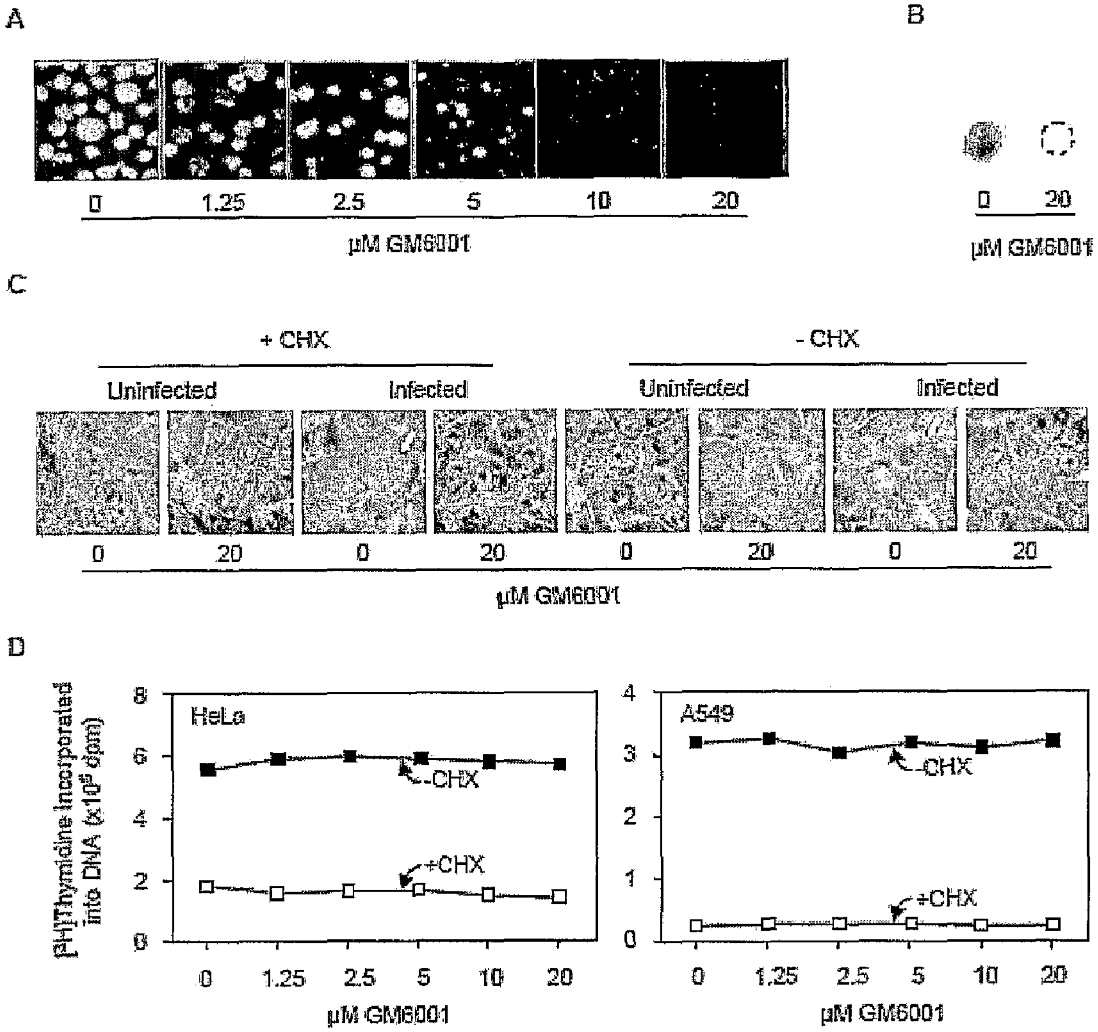
FIGS. 1A-B demonstrates the inhibition of biovar lymphogranuloma growth by GM6001 wherein the culture medium contains 1 μg/ml cycloheximide (CHX) as follows.
FIG. 1C represents live images showing inhibition of inclusion formation by GM6001 in L2-infected HeLa cells cultured with or without cycloheximide, and a lack of cytotoxicity by GM6001 in both uninfected and infected cultures (arrows point to representative inclusions formed without GM6001)
FIG. 1D shows the lack of effects of GM6001 on DNA synthesis in HeLa and A549 cells. (all analyses were made with quadruplicate wells; results varied less than 13%)

The present invention relates to methods and compositions for preventing or treating chlamydial infection with metalloprotease inhibitors. Among the preferred metalloprotease inhibitors are GM6001{N-[(2R-2-(hydroxamidocarbonylmethyl)-4-methylpentanoyl]-L-tryptophanmethylamide}, a hydroxamate that binds to the active site of zinc metalloproteases, and therefore specifically inhibits their enzymatic activities, and TAPI-0 {N-(R)-[2-(Hydroxyaminocarbonyl) methyl]-4-methylpentanoyl-L-naphthylalanyl-L-alanine amide}, which is another hydroxamate that specifically inhibits metalloproteases.

"*Chlamydia*" is used herein to mean any one or more of the bacteria in the genus *Chlamydia*. The genus *Chlamydia* includes the species *C. pneumoniae, C. psittaci* and *C. trachomatis.*

"*Chlamydia* prophylactic effective amount" is used herein to mean that amount which results in a sufficient concentration of the particular compound at an appropriate site to reduce the risk of infection by *Chlamydia*. By appropriate site, it is meant a site that potentially contains *Chlamydia* or is an area of a patient of potential exposure to *Chlamydia* or is an area of a subject that has been exposed to *Chlamydia* but as a result of such exposure, the subject has not yet acquired chlamydial disease.

"Treatment effective amount" is used herein the mean that amount which results in a sufficient concentration of the particular compound at an infected site to therapeutically ameliorate or reduce the effects of the disease.

The compositions used in the instant invention may be applied topically to prevent or treat chlamydial infection. For topical administration, suitable carriers or vehicles include polar, protic solvents, such as, water or normal saline, non-polar solvents, lipids, ointments, jellies, inserts and foaming inserts (suppositories, sponges, and the like) salves, creams, foams, douches, or the like. The compositions may also be suspended in a suspension medium that is not miscible with water, for example, petrolatum, or may be formulated in an emulsion (water-in-oil or oil-in-water). More particularly, the compositions can be applied intravaginally for the prevention or treatment of *Chlamydia*. The topical composition containing the metalloprotease inhibitor could, for example, be applied with an applicator or an intravaginal device or the topical composition could be coated on a male or temale condom or otner sexual barrier devices, such as diaphragms, cervical caps, and the like.

For topical applications, the pharmaceutically acceptable carrier may additionally comprise organic solvents, emulsifiers, gelling agents, moisturizers, stabilizers, surfactants, wetting agents, preservatives, time-release agents, and minor amounts of humectants, sequestering agents, dyes, perfumes, and other components commonly employed in pharmaceutical compositions for topical administration.

Solid dosage forms for topical administration include suppositories, powders, and granules. In solid dosage forms, the compositions may be admixed with at least one inert diluent such as sucrose, lactose, or starch, and may additionally comprise lubricating agents, buffering agents and other components well known to those skilled in the art.

The compositions of the invention may also be impregnated into absorptive substrate materials, such as sponges, or coated onto the surface of solid substrate materials, such as male or female condoms, diaphragms, cervical caps, or medical gloves, to deliver the compositions to vaginal or other potentially injectable epithelium. Other articles and delivery systems of this type will be readily apparent to those skilled in the art.

Among the presently preferred articles are condoms. As used herein, "condom" refers to a barrier device which is used to provide a watertight physical barrier between male and female genitalia during sexual intercourse, and which is removed after intercourse. This term includes conventional condoms, which cover the penis; it also includes so-called "female condoms" which are inserted into the vaginal cavity prior to intercourse. Preferably, condoms should be made of latex or a synthetic plastic material such as polyurethane, since these provide a high degree of protection against viruses.

A method of coating a condom with a composition comprising a metalloprotease inhibitor comprises coating the whole surface or necessary portion of a condom by dropping, dipping, coating or spraying a solution containing a metalloprotease inhibitor. Condom coating methods are well-known, and the metalloprotease inhibitor compositions can be incorporated into the known condom coating compositions, including lubricant compositions. Preferred coating compositions include silicon, which provides lubricity and releases the composition in a time-release manner. In this way, a condom having an anti-Chlamydial effect and a lubricating effect can be obtained. Bioadhesive polymers may also be used to prolong the time-release aspects of the particular topical or other medicament employed. The metalloprotease inhibitor can also be impregnated into the condom during manufacture by processes known in the art.

The amount of the metalloprotease inhibitor applied on one condom can be any amount that provides the desired prophylactic effect with little or no side effects, preferably from about 0.001 mg to about 1000 mg. Coating a condom is carried out on one side or to both the inner surface and the outer one.

The metalloprotease inhibitors used in the present invention for the prevention or treatment of Chlamydial infection are generally administered in such a dosage as to achieve the desired actions with limited or no side effects. Although the actual dosage should be determined according to the judgment of doctors, the preferred concentration in a pharmaceutically acceptable carrier can vary from about 0.00005% to about 5% by weight.

The topical composition may be applied to human or other animal skin or mucous membranes for the prevention of *Chlamydia* or the treatment of various medical conditions associated with Chlamydial infection such as Chlamydial eye diseases, sexually transmitted Chlamydial infections, complications of sexually transmitted Chlamydial infections, and Chlamydial pneumonia.

A prophylactic effective amount of the composition can be applied to the contact site either before or after contact with *Chlamydia*. Preferably, the composition can be applied from about 1 hour before contact with *Chlamydia* to about 6 hours after contact with *Chlamydia*. More preferably, the topical composition is applied within five minutes of contact with *Chlamydia*.

The following non-limiting examples set forth hereinbelow illustrate certain aspects of the invention.

EXAMPLES

Example 1

Inhibition of L2 (Biovar LGV) growth by GM6001

Human cervical carcinoma HeLa cells grown on coverslips were exposed to an EB stock of strain 434/bu of serovar L2 (L2, biovar LGV) for 2 hours, washed to remove free EBs, and cultured in medium containing indicated concentrations of GM6001 plus 1 μg/ml cycloheximide, an inhibitor of eukaryotic protein synthesis which is commonly used to facilitate chlamydial growth. 40 hours later, cells were fixed with methanol, and reacted for 1 hour with a monoclonal antibody against the major outer membrane protein (MOMP) of L2. After three washes with PBS, coverslips were reacted with fluorescein isothiocyanate-conjugated goat anti-mouse IgG (Sigma, St. Louis, Mo.) for 30 min. After additional washes, coverslips were mounted onto glass slides and viewed with a Nikon Eclypse E1000 fluorescent microscope. As shown in FIG. 1A, the number of inclusions declined progressively as the concentration of GM6001 increased.

The inhibition of L2 growth by GM6001 is also demonstrated in the human lung carcinoma A549 cells with dot blot analysis (FIG. 1B). Infection of A549 cells and inhibitor treatment were carried out as described above. 40 hours after infection, cells were lysed in 200 μl of $H_2O$, a 50 μl sample of the resulting EB/RB extract was blotted onto Zeta Probe membrane (Bio-Rad), and sequentially reacted with the L2 MOMP antibody described above, and horseradish peroxidase-conjugated rabbit anti-mouse IgG. Using the ECL kit (Amersham) a strong MOMP signal was detected in untreated culture, whereas no signal was detected in GM6001-treated culture (FIG. 1B).

The inhibition of L2 growth by GM6001 could be viewed directly under a light microscope without immunostaining. Shown in FIG. 1C are images obtained from live cultures. Evidently, GM6001 was effective against chlamydial infection when it was used in both the presence and absence of cycloheximide. In addition, GM6001 showed no apparent cytotoxic effects in either uninfected or L2-infected HeLa cells based on their morphology.

The lack of cytotoxic activity in GM6001 was further supported by measuring DNA synthesis. Subconfluent cells grown in 24 well plates were fed with medium (0.5 ml/well) containing indicated concentrations of GM6001 for 40 hours. 2 μl of [methyl-3H]thymidine (specific activity: 20 Ci/mmole, Moravek Biochemical, Brea, Calif.) was added into the culture and incubated for 2 hours. The amount of thymidine incorporated into DNA was determined as we previously described (3). At concentrations that were effective against L2 infection, GM6001 did not exhibit any inhibitory effect on DNA synthesis in uninfected HeLa and A549 cells (FIG. 1D). As expected, cycloheximide effectively inhibited DNA synthesis activity. However, GM6001 showed no synergistic or additive effect on cycloheximide-induced inhibition of DNA synthesis. Taken together, data presented in FIG. 1 suggest that GM6001 inhibits L2 infection without being noticeably toxic to the host cells.

Example 2

Inhibition of the Growth of Biovar Trachoma and Mouse Biovar by GM6001

Figure 2:
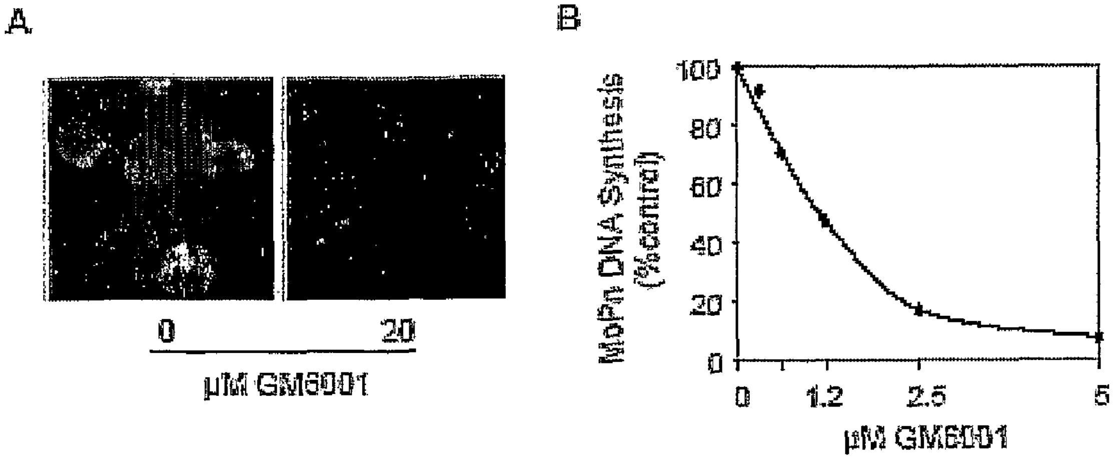
FIGS. 2 A-B demonstrate the inhibition of biovars trachoma and mouse by GM6001 as follows.

We next tested whether GM6001 was also effective against the remaining two biovars of *C. trachomatis*. GM6001 efficiently suppressed inclusion formation by strain UW-3/Cx of serovar D (biovar trachomatis) as shown by immunostaining using a monoclonal antibody that recognizes chlamydial lipopolysacharide (FIG. 2A). The effect of GM6001 on biovar mouse was determined by measuring chlamydial DNA synthesis with procedures that we previously detailed (1, 3). A dose-response curve of GM6001 inhibition of MoPn growth was obtained (FIG. 2B). Thus, our results suggest that GM6001 inhibits the infection of all three *C. trachomatis* biovars in multiple cell types.

Example 3

Inhibition of L2 Growth by TAPI-0

Figure 3:
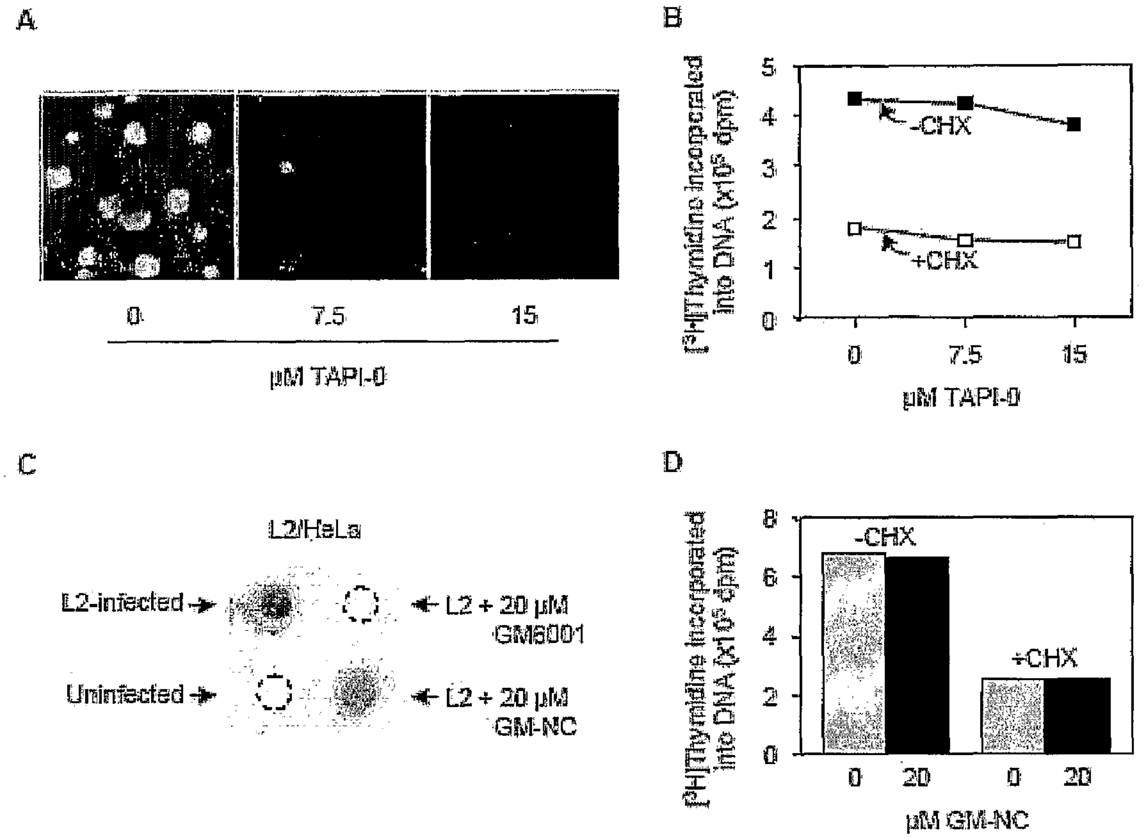
FIGS. 3A-D represent inhibition of L2 growth by TAPI-0, but not by GM6001 Negative Control (GM-NC) as follows.

TAPI-0 strongly inhibited L2 infection at both 7.5 and 15 μM as shown by MOMP immunofluorescence (FIG. 3A), while no cytotoxicity was observed at either concentration as judged by cellular morphology (data not shown) and by DNA synthesis of HeLa cells (FIG. 3B). Therefore, inhibition of chlamydial infection appears to be a common property of hydroxamate-based metalloprotease inhibitors.

Example 4

GM6001 Negative Control

GM6001 Negative Control (N-t-butoxycarbonyl-L-leucyl-L-tryptophan methylamide), a chemical derivate of GM6001, which contains a very minor modification causing a loss of binding to the catalytic center of metalloproteases, had no detectable effect on chlamydial growth (FIG. 3C). These results suggest that GM6001 and TAPI-0 inhibit chlamydial infection by targeting a metalloprotease(s). Similar to GM6001 and TAPI-0, GM6001 Negative Control showed no adverse effect on DNA synthesis (FIG. 3D) and the morphology (data not shown) of HeLa cells.

Example 5

Inhibition Of Host Versus Bacterial Enzymes

Figure 5:
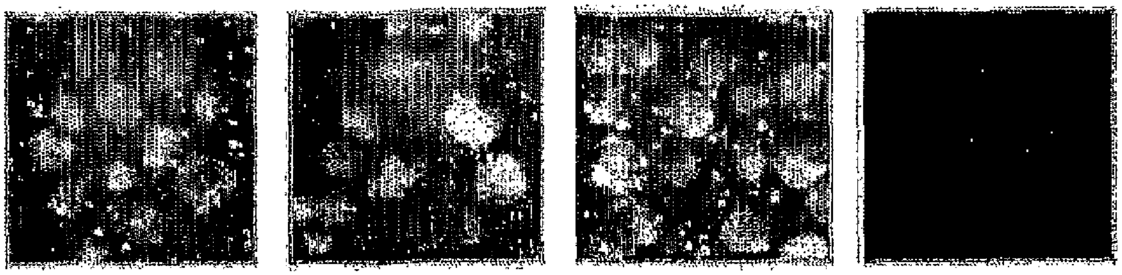
FIG. 5 demonstrates the lack of inhibition of L2 growth by pretreatment of host HeLa cells and EBs with GM6001.

To address whether suppression of chlamydial growth resulted from inhibition of host or bacterial enzymes, we determined the effect of pretreatment of EB and host cells with a hydroxamate on chlamydial growth. HeLa cells were cultured for 2 h with medium containing 20 °μM GM6001 and washed 3 times with medium before they were infected with a regular EB stock. Likewise, an EB stock was also incubated with GM6001, washed, and added to untreated HeLa cells. As control, GM6001 (final concentration: 20 μM) was added into and maintained in the culture medium after the attachment/entry period. Immunostaining showed that the pretreatments were completely ineffective against chlamydial infection (FIG. 5).

Example 6

The Effect of GM6001 and TAPI-0 on the Growth of *Escherichia coli* and *Lactobacillus delbrueckii*

Figure 4:
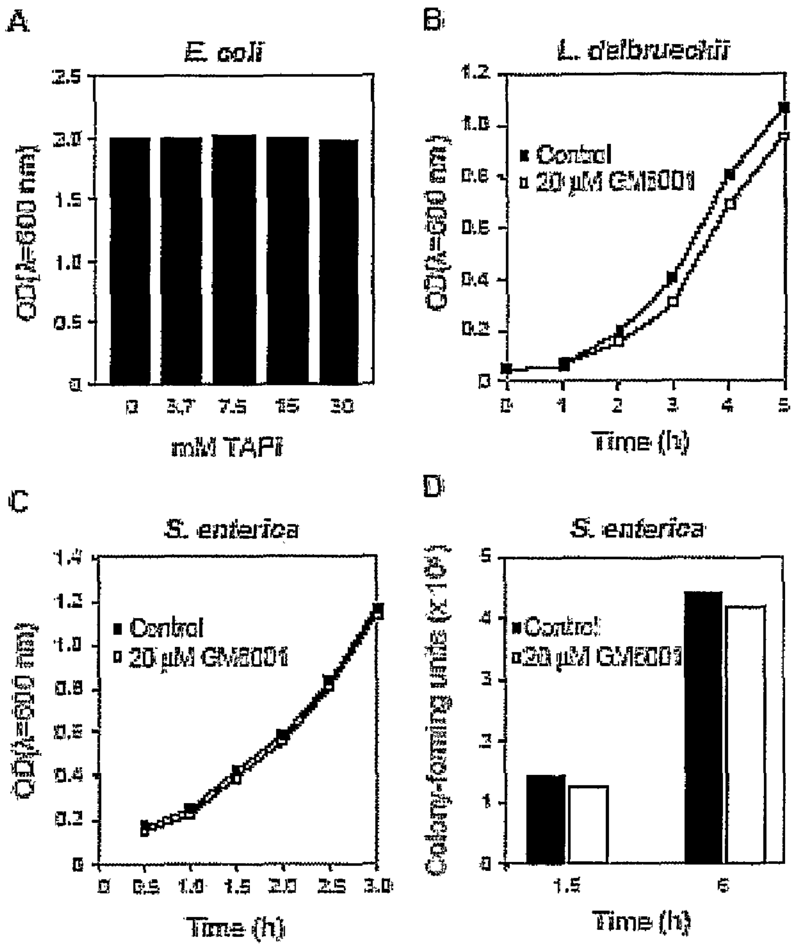
FIGS. 4A-C demonstrate the lack of inhibition by hydroxamates on the growth of *Escherichia coli, Lactobacillus delbrueckii*, and *Salmonella enterica* cultured in liquid media as follows.
FIG. 4D represents the lack of inhibition by GM6001 of *Salmonella enterica growth in HeLa cells;*

An *E. coli* MG1655 colony was inoculated into 10 ml LB broth, which was then divided into 2 ml aliquots. TAPI-0 was added to the aliquots to the final concentrations indicated in FIG. 4A. After overnight culture, $OD_{600}$ measurements were taken. An overnight *L. delbrueckii* (ATCC 12315) culture was diluted 1:100, and cultured in the presence or absence of 20 μM of GM 6001. $OD_{600}$ values were measured hourly up to 5 h postinoculation. The compounds did not show any effects on the growth of *E. coli* and *Lactobacillus delbrueckii* (FIG. 4A and FIG. 4B).

Example 7

The Effect of GM6001 on the Growth of *Salmonella Enterica Serovar Typhimurium*

Like *Clamydiae, S. enterica* also grows inside a vacuole in the cytoplasm of the infected cell although the Salmonella inclusion differs substantially from the clamydial inclusion. GM6001 had no effect on the growth of *S. enterica* when it was cultured as a free-living organism in liquid medium (FIG. 4C). To assess whether its intracellular growth is affected by the inhibitor, HeLa cells were infected with a fresh culture of *S. enterica* grown to stationary phase as previously described (16). After washes to remove free bacteria, the cells were cultured with medium containing 50 μg/ml gentamycin (to kill any residual free bacteria) plus or minus 20 μM GM6001 for 1.5 and 6 h. Gentamycin was then removed by washes. Intracellular bacteria were released by 0.1% Triton X-100, serially diluted and plated onto LB agar plates. After overnight incubation at 37° C., colony-forming units were scored. GM6001 did not inhibit the growth of *S. enterica* inside HeLa cells (FIG. 2D). Therefore, hydroxamate-based metalloprotease inhibitors appear to specifically inhibit *Chlamydiae* without affecting the growth of facultative intracellular or free-living bacteria.

Inhibition of chlamydial growth was obtained when GM6001 and TAPI-0 was added to cultures at the end of the two hour attachment/entry period (FIGS. 1-3), a point where free unbound EBs had been removed by extensive washes. The entry-independent inhibition was also seen by titrating infectious EBs produced by infected HeLa cells (FIG. 6). Accordingly, 20 μM GM6001, added at the end of attachment/entry period, exhibited a better than 99.99% inhibition of EB production. A comparable inhibitory activity was also noted when GM6001 was added 8 h after infection. At this point, EBs have already completed the entry phase and have differentiated into RBs in inclusions. Even when GM6001 treatment was started 24 h after infection, a point where the number of RBs peaks during the chlamydial developmental cycle, a 99% reduction in EB production was observed (FIG. 6). These results indicate that GM6001 inhibits chlamydial infection by blocking a step(s) subsequent to EB entry.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the spirit and script of the invention, and all such variations are intended to be included within the scope of the following claims.

What is claimed is:

1. A method for treating chlamydial infection comprising applying a treatment effective amount of a hydroxamate metalloprotease inhibitor to a portion of a patient's body infected by *Chlamydia*.

2. The method of claim 1 wherein said metalloprotease inhibitor is selected from the group consisting of N-[(2R)-2-(hydroxamidocarbonylmethyl)-4-methylpentanoyl]-L-tryptophan methylamide and N-(R)-[2-(hydroxyaminocarbonyl)methyl]-4-methylpentanoyl-L-naphthylalanyl-L-alanine amide.

3. The method of claim 1 wherein said metalloprotease inhibitor is from about 0.00005% to about 5% by weight of the composition.

4. The method of claim 1 wherein said metalloprotease inhibitor is incorporated into a topical composition comprising a pharmaceutically acceptable aqueous solution, non-aqueous solution, suspension, ointment, jelly, insert, suppository, sponge, salve, cream, foam, foaming tablet, or douche.

5. The method of claim 1 wherein the composition is applied intravaginally.

6. The method of claim 1 wherein the composition is applied from about 1 hour before to about 6 hours after exposure to *Chlamydia*.

7. The method of claim 1 wherein the composition is applied with an applicator or an intravaginal delivery device.

8. The method of claim 7 wherein the applicator or intravaginal delivery device is a barrier contraceptive.

9. The method of claim 1 wherein the chlamydial infection is selected from the group consisting of chlamydial eye diseases, sexually transmitted chlamydial infections, complications of sexually transmitted chlamydial infections, and chlamydial pneumonia.

10. A method for treating *Chlamydia* infection in a subject at risk comprising (a) applying a topical composition comprising an effective amount of a hydroxamate metalloprotease inhibitor to an area of said subject at risk for exposure to *Chlamydia*, and (b) inhibiting *Chlamydia* growth in said area.

11. A method for treating *Chlamydia* infection in a subject in need thereof comprising (a) identifying a subject suffering from *Chlamydia* infection, (b) topically applying a composition comprising an effective amount of a hydroxamate metalloprotease inhibitor and a pharmaceutically acceptable carrier to an area of said subject infected with *Chlamydia*.

12. The method of claim 2, 10, or 11 wherein said hydroxamate metalloprotease inhibitor is N-[(2R)-2-(hydroxamidocarbonylmethyl)-4-methylpentanoyl]-L -tryptophanmethylamide.

* * * * *